United States Patent [19]

Macri

[11] Patent Number: 5,528,521
[45] Date of Patent: Jun. 18, 1996

[54] TITRATION EMULATION SYSTEM AND METHOD

[75] Inventor: Timothy F. Macri, Chapel Hill, N.C.

[73] Assignee: Hoffmann-La Roche Inc., Nutley, N.J.

[21] Appl. No.: 250,246

[22] Filed: May 27, 1994

[51] Int. Cl.$^6$ .................................................. G01N 21/79
[52] U.S. Cl. ..................... 364/571.04; 364/497; 356/410
[58] Field of Search .......................... 364/571.01, 571.07, 364/577, 496–499, 579, 580, 497, 571.02, 571.04; 422/75, 63, 67, 68.1; 73/1 R; 204/400, 405; 250/565; 354/412; 356/409, 410, 436

[56] References Cited

U.S. PATENT DOCUMENTS

| | | | |
|---|---|---|---|
| 3,975,727 | 8/1976 | Mader et al. | 73/1 R |
| 3,988,591 | 10/1976 | Killer | 356/36 |
| 4,043,756 | 8/1977 | Sommervold | 364/571.04 |
| 4,058,365 | 11/1977 | Krogh | 436/51 |
| 4,180,440 | 12/1979 | Gibboney et al. | 205/788.5 |
| 4,266,942 | 5/1981 | Vandenbossche et al. | 364/497 |
| 4,411,988 | 10/1983 | Toth et al. | 435/7.1 |
| 4,528,267 | 7/1985 | Calenoff et al. | 435/7.92 |
| 4,573,195 | 2/1986 | de France | 382/6 |
| 4,697,236 | 9/1987 | Butts et al. | 364/413.07 |
| 4,948,975 | 8/1990 | Erwin et al. | 250/361 C |
| 5,125,748 | 6/1992 | Bjornson et al. | 356/414 |
| 5,187,749 | 2/1993 | Sugimoto et al. | 364/413.08 |
| 5,192,509 | 3/1993 | Surjaatmadja et al. | 422/75 |
| 5,373,366 | 12/1994 | Bowers | 356/435 |

FOREIGN PATENT DOCUMENTS

| | | |
|---|---|---|
| 2105727 | 3/1994 | Canada . |
| 87104078 | 1/1988 | China . |
| 012698 | 12/1979 | European Pat. Off. . |
| 017909 | 10/1980 | European Pat. Off. . |
| 97160 | 6/1989 | Romania . |
| 88/01380 | 2/1988 | WIPO . |

OTHER PUBLICATIONS

Nakano Sumise K.K., Automatic Titration Device, Mar. 4, 1994, Abstract only.

*Primary Examiner*—James P. Trammell
*Assistant Examiner*—Craig Steven Miller
*Attorney, Agent, or Firm*—George M. Gould; George W. Johnston; John P. Parise

[57] ABSTRACT

A method and system achieving the results of a conventional titration without the need to chemically dilute a sample. Such a result is accomplished by providing a plurality of calibration standards, each containing a different known concentration of a visualizable material. The visualizable material contained within each calibration standard is then visualized (the parameters of the visualization forming a setting). The visualization is then altered by adjusting at least one parameter of the visualization until the point where the visualizable material within each calibration standard can no longer be visualized in the solution. The visualizable material within a sample solution having an Unknown concentration of the visualizable material is then visualized using settings corresponding to the plurality of calibration standards to generate a number of modified visualizations. (Each modified visualization corresponds to the concentration of the standard to which it relates). The modified visualization at which point the visualizable material can no longer be visualized is then correlated with the corresponding concentration, to determine the titration of the sample solution.

23 Claims, 4 Drawing Sheets

TITRATION EMULATION PROCESS

TITRATION EMULATION SYSTEM AND METHOD

FIELD OF THE INVENTION

The present invention relates to a system and method for achieving the results of conventional titration without chemical dilution of a sample (hereinafter referred to as "titration emulation").

BACKGROUND OF THE INVENTION

Conventional titration involves serially diluting a liquid sample, and then analyzing the series of diluted samples to identify the most dilute sample which still evidences the tested-for parameter (the endpoint). Titration emulation is useful for performing titrations where the intensity of the initial titer is functionally related to the titration endpoint. One such application is fluorescent microscopy, such as used in fluorescent anti-nuclear antibody (FANA) testing.

For tests such as FANA, conventional titration involves serially diluting samples and then placing the diluted samples under a fluorescent microscope to manually evaluate each dilution and identify the most dilute sample which exhibits fluorescence. Unfortunately, this method is time consuming, arguous, material intensive and expensive.

Moreover, in addition to ANA concentration level, there are six discernible morphologic patterns associated with immunofluorescent staining. Some morphologic patterns are clinically significant. Accordingly, a sample must be visually examined in supplement to endpoint determination. Since titration emulation evaluates a single sample containing a screening dilution (typically 1:40) information, only one sample needs review to determine both endpoint and morphologic patterns.

As descried in the present specification, titration emulation typically produces a series of images corresponding to the initially diluted sample. Each image is formed from a combination of image component parameters, such as brightness, contrast and exposure time, which provides an effective level of intensity sensitivity. Parameters are adjusted such that each produced image emulates the effect of a successive dilution. Appropriate parameters and their settings for each titer are determined by calibrating to an acceptable standard.

The subject titration emulation in its preferred form presents a technician with a series of images analogous to the series of conventional dilutions he is accustomed to evaluating. Accordingly, a technician familiar with seeing dilutions at 1:40, 1:80, 1:160, 1:320, 1:640, 1:1280, 1:2560, and 1:5120 would be presented with eight images corresponding to these dilutions. The technician's job essentially remains the same: choose the image corresponding to the titer at which the tested-for material is no longer visible (the endpoint).

The above process can be automated to eliminate the technician. For example, a signal corresponding to each "dilution" may be compared by computer, with an automated cytology analysis system (such as Roche's Autocyte System described in patent application Ser. No. 08/135,640, filed Oct. 12, 1993, now abandoned the contents of which are herein incorporated by reference) being used to evaluate morphology. However, it is presently preferred to retain the use of a technician both as a quality control and to evaluate pattern morphology.

The number of dilutions may be varied by either evaluating varying numbers of standards, or interpolating and/or extrapolating results obtained from tested standards to generate "theoretical dilutions." Such theoretical dilutions can provide a continuum which may yield greater accuracy in reporting titrations.

Advantages of this new titration emulation system and method include cost reduction, higher throughput, more accurate measurement, minimal fading, and ease of use. No physical liter is required, thus fewer slides are needed. Accurate measurement is obtained because calibration reduces subjectivity and provides consistency between runs. Additionally, computer controlled exposure minimizes fading of the fluorescent material. Lastly, use of the system and method is simple, because the concepts involved are readily understood by those familiar with conventional titration analysis.

SUMMARY OF THE INVENTION

The subject invention provides a titration emulation system and a method for titration emulation of a sample solution.

The subject system includes a detector for visualizing the sample in accordance with predetermined visualization parameters. The visualization parameters for each sample visualization form a setting. Means for generating a digital visualization signal corresponding to the detector's visualization of the sample are provided, as are means for altering the visualization parameters used to generate the digital visualization signal. Means for storing the settings for the visualization parameters, and means for generating a modified digital visualization signal by altering the visualization parameters according to the settings stored by the storage means, are also provided. Additionally provided are means for evaluating the modified digital visualization signal.

The term "altering" refers to an adjustment of at least one parameter of the visualization of a sample, and includes analog adjustments, such as gain, and digital adjustments, such as brightness and contrast.

Typically, the detector is an analog video camera used together with means for converting analog signals to digital signals. However, a digital video camera may be used. Means for evaluating the digital visualization signals generally include a computer with a cathode ray tube (CRT) monitor, and means for generating a digital signal typically comprise an imaging board.

Preferably, the system includes a microscope, such as a fluorescence microscope, which is optically coupled with the camera.

The subject invention also provides a method for titration emulation of a sample solution. This method involves several steps, the first step is providing a plurality of calibration standards, each containing a different known concentration of a visualizable material. The second step is visualizing the visualizable material contained within each calibration standard, the parameters of each visualization forming a setting. The third step is, for each calibration standard, altering the visualization of the material contained within the calibration standard by adjusting at least one parameter of the visualization of the calibration standard until the point where the visualizable material within the calibration standard can no longer be visualized within the solution. The settings corresponding to the plurality of calibration standards may be interpolated or extrapolated from the settings for each calibration standard visualized. Thus, the term "each of the settings" is to include additional interpolated or extrapolated setting. The fourth step is visualizing the visualizable material within a sample solution having an unknown concentration of the visualizable material using each of the settings which correspond to each of the plurality of calibration standards, to generate a number of modified visualizations which corresponds to the concentration of the calibration standard to which each modified visualization relates. The fifth step is correlating the modified visualization to the point at which the visualizable material can no longer be visualized with the corresponding concentration of visualization material, thereby determining the titration endpoint of the sample solution.

In a preferred embodiment, plurality of calibration standards comprises (i) providing a plurality of standard solutions, each having a different concentration of the visualizable material, (ii) reducing the concentration of the visualizable material within each standard solution until the concentration of the visualizable material is such that the visualizable material can no longer be visualized within each resulting solution, and (iii) determining the concentration at which the visualizable material can no longer be visualized within each of the resulting solutions.

Generally, the visualizable material is a fluorescent material, and the parameters of the visualization typically comprise exposure time, contrast and brightness. However, the parameters of the visualization may be based upon an exposure time value. Exposure time value is a combination of exposure time and at least one other visualization parameter, such as an analog or digital adjustment to the exposure time. Additionally, the plurality of calibration standards is typically provided by serial dilution of a visualizable material of known concentration

BRIEF DESCRIPTION OF THE FIGURES

FIG. 2B—A schematic of preferred components of the titration emulation system.

DETAILED DESCRIPTION OF THE INVENTION

Figure 1:
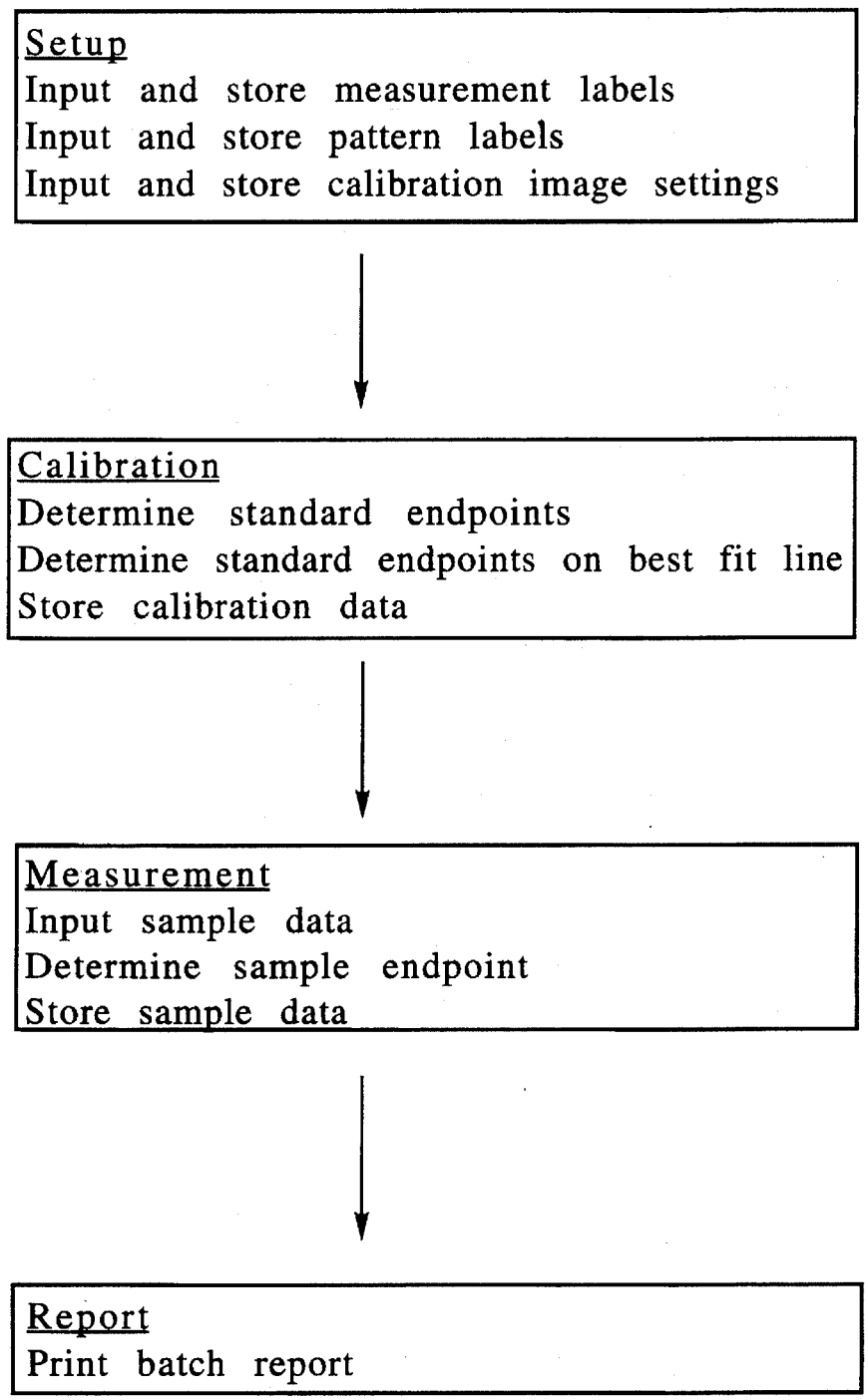
FIG. 1—A schematic depicting the steps of the titration emulation process.
Figure 2A:
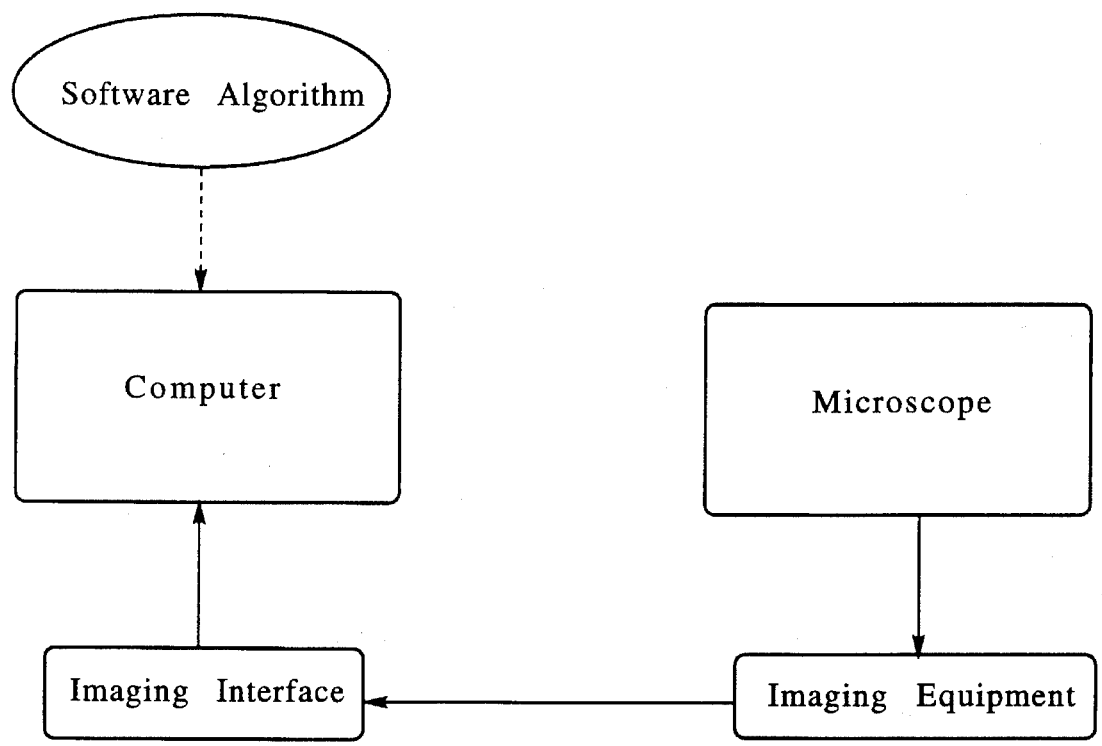
FIG. 2A—A schematic of required components of the titration emulation system.
Figure 2B:
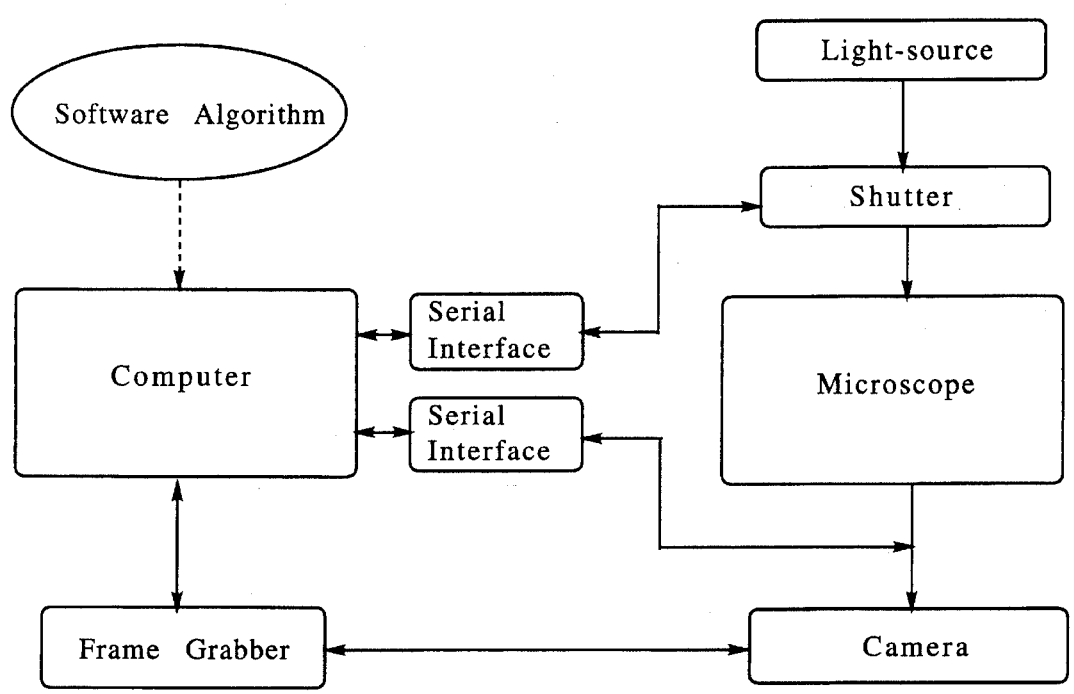

The invention will now be described in the terms of its preferred embodiments. These embodiments are set forth to aid in the understanding of the invention, but are not to be construed as limiting.

Although the subject system and method are adaptable to numerous procedures which are readily determinable to the skilled artisan, to facilitate understanding, the invention will be described relative to a FANA test. FANA test procedure is described in the brochure Clinical. Lab Products, July 1984, *ANA testing*, by Susan L. Retka of Kaloestad Laboratories, the contents of which are herein incorporated by reference. In brief:

An amount of patient serum is mixed with a suitable buffer to form a solution having a known dilution. For example, a typical screening dilution is 1:40 serum to buffer. A sample of this solution is pipetted to one well on an ANA slide. (An ANA slide has a plurality of wells (typically ten or twelve) containing a substrate (usually human epithelial [HEp-2 cells]) that serves an antigen for the anti-nuclear antibody). Each slide undergoes a series of incubations and washings. During this process, anti-nuclear antibodies are indirectly tagged with a fluorescent dye. Each well is then viewed for immunofluorescence using a fluorescent microscope. ANA concentration is directly related to fluorescent intensity.

All slides prepared and processed together are referred to as an ANA batch or run. Each batch includes a calibration slide, a control slide, and patient slides. Although there is a set procedure to ensure consistent processing of the slides, there can be significant differences from batch to batch due to variations in equipment, materials, and procedural errors.

Generally, a FANA test has two phases. The first phase is screening. Each patient's serum sample is tested for positive or negative immunofluorescence (typical screening dilution is 1:40). If immunofluorescence is visible in the screening dilution, the sample is positive, if not it is negative. For the screening phase, only one well is required for each patient.

The second phase is titration. End point titration is performed for each sample identified as positive in the screening phase, typical titration dilutions are 1:40, 1:80, 1:160, 1:320, 1:640, 1:1280, and 1:2560, and 1:5120. The end point occurs at the last dilution where immunofluorescence is still clearly visible. For example, if immunofluorescence is present in 1:320 dilution, and no immunofluorescence is present in the 1:640 dilution, the end point is 1:320.

The following hardware components are used in the subject titration emulation system: a video camera, having suitable interface and control parameter ability; an imaging "board" with video frame grabbing capability; a computer with suitable imaging and interface capability; a microscope with fluorescence capability and TV camera interface, and shutter having suitable interface. One suitable system uses an Optronics DEI-470 video camera with serial interface, a Kontron frame grabber imaging board, a 486 PC compatible computer, and a Zeiss Axioskop microscope with HBO 100 W/2 fluorescent package, FITC filter set (fluorescein stain) and trinocular head, or alternatively, a Nikon Labophot with HBO 100 watt fluorescent package, FITC filter set (fluorescein stain) and trinocular head.

The preferred system employs software which coordinates the four major steps of the subject invention: setup, calibration, measurement, and report. The software useful in connection with the subject invention is readily determinable to the skilled artisan who has reviewed the instant specification. Setup involves input and storage of measurement labels, pattern labels, and calibration image settings. Calibration determines standard sample endpoints, then applies the endpoints to a best fit line or non-linear curve, and stores the calibration data. Measurement inputs patient sample data, determines each patient's sample endpoint, and stores each patient's sample data. Report is a data summarization which may be a printed batch, video screen, or other summary.

Setup

A first step in the subject method is setup. Setup tailors the inventive process to suit a customer's specific needs. The main task of setup, "input and store measurement labels, pattern labels, and calibration image settings," is usually performed only once at product installation.

Measurement labels are stored in the "Measurement Label Table," and are used to label the images presented to the user during the measurement step (typically 8 images are used). Each label corresponds to one standard of a calibration slide.

The following example illustrates appropriate values for a calibration based on titer standards (CDC) in which 8 dilutions are used to form the titer. Alternatively, calibration may be based on IU/ml standards (WHO) with the images labeled with appropriate IU/ml values.

Measurement Label Table

| Standard | Label |
|---|---|
| 1 | 1:40 |
| 2 | 1:80 |
| 3 | 1:160 |
| 4 | 1:320 |
| 5 | 1:640 |
| 6 | 1:1280 |
| 7 | 1:2560 |
| 8 | 1:5120 |

Measurement Display

| 1 | 2 | 3 | 4 |
|---|---|---|---|
| 1:40 | 1:80 | 1:160 | 1:320 |

| 5 | 6 | 7 | 8 |
|---|---|---|---|
| 1:640 | 1:1280 | 1:2560 | 1:5120 |

Calibration image settings are stored in the "Calibration Settings Table." These settings correspond to the 16 calibration images presented to the user during the calibration step. Three parameters are currently stored for each image: "Exposure Time," "Contrast" and "Brightness." Of course, additional or alternative parameters may be used. Exposure Time (generally in seconds) is the time period over which an image is integrated. Brightness (in relative units) is a digital intensity offset adjustment used as an effective intensity threshold. Contrast (in relative units) is a digital intensity gain adjustment used to control the effective dynamic range of the intensity. Analog adjustments, such as gain, and digital adjustments, such as brightness and contrast, may be used to modify the video signal of an image acquired at a certain exposure time in order to simulate an image acquired at a slightly different exposure time. Thus, it is an object of the invention to present the user with a uniform gradient of images spanning a wide enough dynamic range for the intended application. The example below shows experimental values used during the research phase of this project for the FANA application.

Calibration Settings Table

| Image | Exposure Time (sec) | Brightness | Contrast |
|---|---|---|---|
| 1 | ¼ | 0 | 0 |
| 2 | ¼ | −3 | −1 |
| 3 | ¼ | −5 | −2 |
| 4 | ¼ | −8 | −3 |
| 5 | ⅛ | 0 | 0 |
| 6 | ⅛ | −3 | −1 |
| 7 | ⅛ | −5 | −2 |
| 8 | ⅛ | −8 | −3 |
| 9 | 1/15 | 0 | 0 |
| 10 | 1/15 | −3 | −1 |
| 11 | 1/15 | −5 | −2 |
| 12 | 1/15 | −8 | −3 |
| 13 | 1/30 | 0 | 0 |
| 14 | 1/30 | −3 | −1 |
| 15 | 1/30 | −5 | −2 |
| 16 | 1/30 | −8 | −3 |

Calibration Display

|  | 0, 0 | −1, −3 | −2, −5 | −3, −8 |
|---|---|---|---|---|
| ¼ | 1 | 2 | 3 | 4 |
| ⅛ | 5 | 6 | 7 | 8 |
| 1/15 | 9 | 10 | 11 | 12 |
| 1/30 | 13 | 14 | 15 | 16 |

Calibration

The second step of the subject procedure is calibration. Calibration determines the image "Endpoint" for each standard sample on the calibration slide and stores each corresponding setting as a calibration value. Calibration values are used in creating the image gradient presented to the user in the "Measurement Display." A set of control samples is used to check calibration. Calibration is preferably performed at the beginning of each batch.

At the beginning of each batch, the user typically enters the batch number and his or her name. Current date and time are automatically recorded by the system. For example see the sample report latter in the text.

Calibration and control slides are prepared and processed along with the patient samples for each batch. The calibration slide contains a gradient of 8 different samples of known ANA concentration. As can be appreciated, fewer than 8 samples can be used to form a gradient. Even two points can be interpolated and/or extrapolated to form a gradient. Each sample is a secondary standard matched to a recognized primary standard sample, such as available from the CDC or WHO. The control slide contains a sample of the same 8 standards, but in scrambled order.

Calibration values are stored in the "Calibration Table." An image Endpoint value and Linear Fit value are determined for each of the 8 standards on the calibration slide. See for example the sample report latter in the text.

For each standard sample, the user selects a field of view and focuses the image on the image monitor. At the user's command, the system acquires a set of 16 images using the settings stored in the Calibration Settings Table (see Setup). The user is presented with the Calibration Display (see Setup) and selects the image endpoint for the sample. The image endpoint is the last image that has clearly visible immunofluorescence. A reference to the settings corresponding to the selected image endpoint is stored in the Calibration Table. This process is performed for each standard sample on the calibration slide.

In the example below, calibration is done using a titer standard with a range of 1:40 to 1:5120. Endpoint and Linear Fit values of the Calibration Table and the numbers in the boxes of the measurement display are calibration image reference numbers (1–16).

Calibration Table

| Standard | Endpoint | Linear Fit |
|---|---|---|
| 1 | 2 | 2 |
| 2 | 3 | 4 |
| 3 | 5 | 6 |
| 4 | 9 | 8 |
| 5 | 11 | 10 |
| 6 | 11 | 12 |
| 7 | 13 | 14 |
| 8 | 16 | 16 |

Measurement Display

| 2 | 4 | 6 | 8 |
|---|---|---|---|
| 1:40 | 1:80 | 1:160 | 1:320 |
| 10 | 12 | 14 | 16 |
| 1:640 | 1:1280 | 1:2560 | 1:5120 |

Linear Fit value can be determined by an algorithm normally encoded on computer software. Linear regression (e.g., method of least squares) may be performed on the 8 image Endpoint values to determine the best fit line. Linear Fit value is the intersection of the vertical line drawn through the Endpoint value and the best fit line. Settings for best fit image are used to acquire the measurement image for the associated standard. A non-linear curve may also be used.

Standards on the control slide are measured in the same way as patient samples using the calibration values. These measurements are used to verify the measurement capability of the system after calibration by comparing the measurement values to the actual values of the control samples.

In the example below, the order of the standards on the control slide is 2,7,4,5,6,3,8,1. In the case shown, the measured endpoint agrees with the calibration value for each standard on the control slide. The Measured Endpoint value of the Control Table and numbers in the boxes of the Measurement Display are standard reference numbers (1–8).

Control Table

| Standard | Measured Endpoint |
|---|---|
| 2 | 2 |
| 7 | 7 |
| 4 | 4 |
| 5 | 5 |
| 6 | 6 |
| 3 | 3 |
| 8 | 8 |
| 1 | 1 |

Measurement Display

| 1 | 2 | 3 | 4 |
|---|---|---|---|
| 1:40 | 1:80 | 1:160 | 1:320 |
| 5 | 6 | 7 | 8 |
| 1:640 | 1:1280 | 1:2560 | 1:5120 |

Measurement

The third step of the subject procedure is Measurement. Measurement inputs patient data, determines the image endpoint, and stores data for each patient sample in the batch.

For each sample, the user inputs a sample ID, pattern, and optional comment. Sample number is a positive integer representing sample position within the batch. The first sample of the batch is 1, the second is 2, and so on. Sample number should be automatically incremented with the option to repeat or skip a sample. The pattern is a fixed text string that is selected by the user from a set of possible morphologic patterns. The optional comment may be a large text field that is entered by the user. For example, see below:

| Sample data: | Sample ID | Measured Endpoint | Pattern | Comment |
|---|---|---|---|---|

For each sample, the user selects a field of view and focuses the image on the image monitor. At the user's command, the system acquires a set of 8 images using the settings stored in the Calibration Table (see Calibration). The user is presented with the Measurement Display (see Calibration) and selects the image endpoint for the sample. Image endpoint is the last image having clearly visible immunofluorescence. The corresponding label of the selected image endpoint is stored in the sample record of the Measurement Table. This process is performed for each sample in the batch.

In the example report later in the text, the Measurement Table (Sample Data) presents 6 samples having various results.

Endpoint may be afforded a standard reference number (1–8) with special values for negative (0) and offscale (9). Labels for these measurement results may be stored in the Measurement Label Table (these labels are not shown in the table in Setup). In the example, negative is labeled Negative and off-scale is labeled >1:5120.

The pattern is also a reference number to a label. The pattern labels are stored in a Pattern Label Table similar to the Measurement Label Table (described in Setup).

Comment is either a text field in the sample record or a pointer to a file containing the text. Implementation of the comment field is dependent on the field size requirement, which needs to be determined.

Report

The fourth and last step of the subject procedure is Report. Report is the end result of the subject method, and contains batch data, calibration data, control and sample data. A goal is to produce a valid report with minimal work. That is, acceptable accuracy in the shortest time possible.

Clinical labs often times have set requirements for how a report should appear. Accordingly, data and its placement in the report should be configurable to satisfy user needs. Thus, a flexible report generator is preferred, as is an interface for an external product serving the same purpose. For example, a system such as MICROSOFT WINDOWS which supports a wide variety of tools, may be incorporated to support the subject software.

The following is an example report:

Batch Report

| Batch number: | Tech name: | Date: | Time: |
|---|---|---|---|

Calibration Data

| Standard | Endpoint |
|---|---|
| 1:40 | 2 |
| 1:80 | 4 |
| 1:160 | 6 |
| 1:320 | 8 |
| 1:640 | 10 |
| 1:1280 | 12 |
| 1:2560 | 14 |
| 1:5120 | 16 |

Sample Data

| Sample ID | Endpoint | Pattern | Comment |
|---|---|---|---|
| 1 | 1:640 | Homogeneous | |
| 2 | 1:160 | Speckled | |
| 3 | 1:1280 | Nucleolar | |
| 4 | 1:40 | Centromere | Difficult to determine pattern. |
| 5 | Negative | NA | |
| 6 | >1:5120 | Homogeneous | Extremely bright |

Software Architecture

Figure 3:
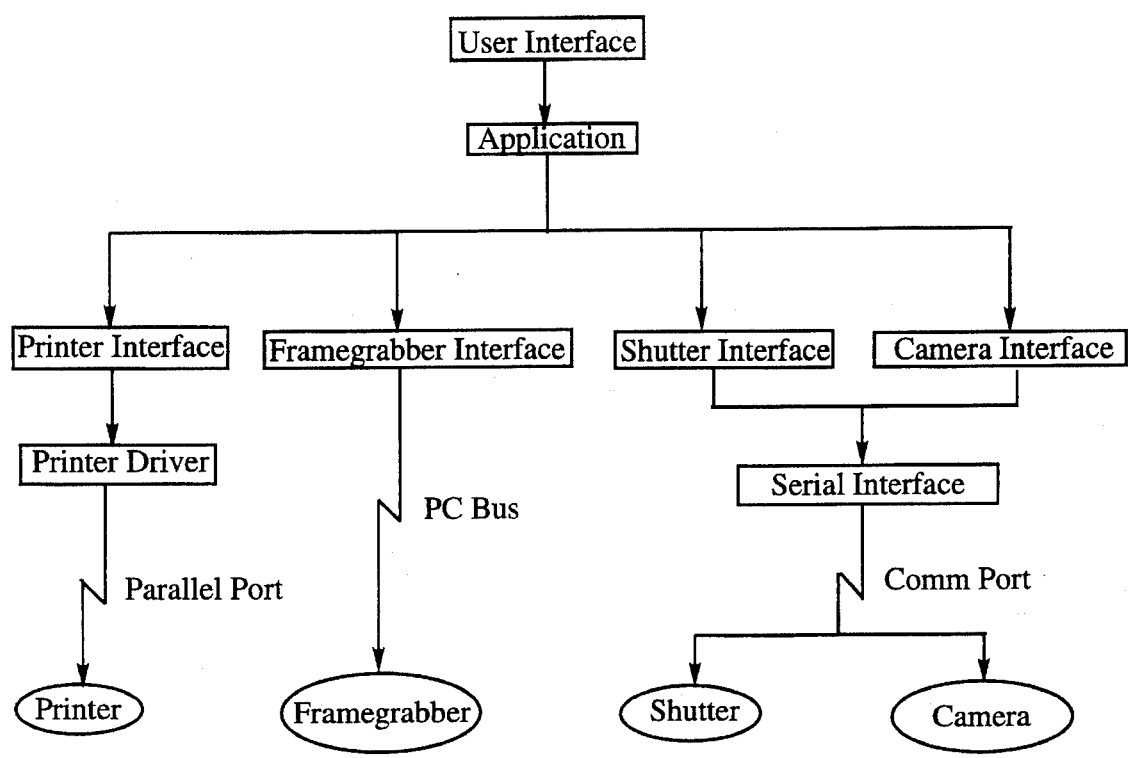
FIG. 3— A schematic showing the software architecture.

The software is organized in a hierarchical structure that isolates each component interface in a single module or set of modules. FIG. 3 shows a preferred architecture for the software.

User Interface

The currently preferred software is utilized in connection with MICROSOFT WINDOWS, and all direct interaction with the user is isolated in this layer. Calls are made to functions in the Application Layer to carry out steps of the procedure.

Application

The application layer contains functions that implement steps of the procedure. All application algorithms are isolated in this layer. Calls are made to the appropriate interface module to interact with specific hardware components.

Camera Interface

This module contains all functions that interact with the camera. Calls are made to the Serial Interface module to communicate with the camera through a Serial Communication Port.

Framegrabber Interface

This module contains all functions that interact with the framegrabber. The CPU communicates directly with the framegrabber over the PC bus.

Shutter Interface

This module contains all functions that interact with the automatic shutter. Calls are made to the Serial Interface module to communicate with the shutter through a Serial Communication Port.

Printer Interface

This module contains all functions that interact with the printer. Calls are made to the printer driver to communicate with the printer through a Parallel Port.

Serial Interface

This module contains all functions that interact with a serial communication port. All direct interaction with a serial communication port is accomplished by calling a function in this module.

Printer Driver

This module contains printer dependent commands. All direct interaction with the printer via the Parallel Port is accomplished through this module.

EXAMPLE 1

A study was conducted to evaluate the measurement performance of the subject system for ANA testing. A complete set of homogeneous samples from a conventional ANA test batch were measured using both the subject system and conventional endpoint titration. A correlation value was determined by directly comparing the results from these two methods of measurement.

The key components of the tested system, all of which are commercially available, were:

486 PC compatible computer

Kontron frame grabber board

Optronics DEI-470 low-light RGB camera with serial interface

UniBlitz VS25 shutter and D122 shutter driver with serial interface

Nikon Labophot with HBO 100W fluorescence package and trinocular head

Filter set for FITC stain

Fluorescence 40x/0.65 objective

The foot switch, previously described in the specification, was not incorporated in this version of the system. This hardware component is not essential to the goals of this study.

An experimental calibration serum was used to calibrate the subject system. A calibration slide was prepared by tittering a sample of the calibration serum using the standard ANA procedure. This slide was processed in the same batch as the study samples. The experimental serum has a known endpoint of 1:1280 which was confirmed by conventional titration as part of the study.

The following table contains the calibration settings used for this study:

| Image | Exposure (sec) | Contrast | Brightness |
|---|---|---|---|
| 1 | ½ | 0 | 0 |
| 2 | ½ | −2 | −4 |
| 3 | ½ | −4 | −8 |
| 4 | ½ | −6 | −12 |
| 5 | ½ | −8 | −16 |
| 6 | ½ | −10 | −20 |
| 7 | ½ | −12 | −24 |
| 8 | ½ | −14 | −28 |
| 9 | ⅟₁₅ | 0 | 0 |
| 10 | ⅟₁₅ | −2 | −4 |
| 11 | ⅟₁₅ | −4 | −8 |
| 12 | ⅟₁₅ | −6 | −12 |
| 13 | ⅟₁₅ | −8 | −16 |
| 14 | ⅟₁₅ | −10 | −20 |
| 15 | ⅟₁₅ | −12 | −24 |
| 16 | ⅟₁₅ | −14 | −28 |

To calibrate the subject system, the wells on the calibration slide were set up in the following way. Since the calibration serum has a known endpoint of 1:1280, the sixth well which was a dilution of 1:1280 was used to calibrate the 1:40 image, the fifth well which was a dilution of 1:640 was used to calibrate the 1:80 image and so on. The first well, which had a dilution of 1:40, was used to calibrate the 1:1280 image, the second well, which had a dilution of 1:80, was used to calibrate the 1:640 image and so on. In effect, the titer to calibrate the system was reversed. The 1:2560 and 1:5120 images were calibrated by extrapolation during a linear fit step. Presently, this is the standard method to calibrate the present system.

The following calibration data was obtained using the calibration slide, in the manner described, and the above settings:

| Titer | End Point |
|---|---|
| 1:40 | 1 |
| 1:80 | 3 |
| 1:160 | 5 |
| 1:320 | 7 |
| 1:640 | 10 |
| 1:1280 | 12 |
| 1:2560 | 14 |
| 1:5120 | 16 |

Results

The following table contains the measurement data from the study:

| Sample | Image Titer Endpoint (Present System) | Endpoint (Conventional Titration) |
|---|---|---|
| 1 | 1:160/1:320 | 1:80 |
| 2 | 1:320 | 1:320 |
| 3 | 1:320 | 1:320 |
| 4 | 1:160 | 1:80 |
| 5 | 1:320 | 1:160 |
| 6 | 1:1280 | 1:1280 |
| 7 | 1:320/1:640 | 1:640 |
| 8 | 1:160 | 1:80 |
| 9 | 1:640 | 1:640 |
| 10 | 1:640 | 1:1280 |
| 11 | 1:160/1:320 | 1:80 |
| 12 | 1:160 | 1:80 |
| 13 | 1:320 | 1:160 |
| 14 | 1:160/1:320 | 1:160 |
| 15 | 1:160 | 1:80 |
| 16 | 1:320 | 1:160 |
| 17 | 1:640 | 1:320 |
| 18 | 1:640 | 1:320 |
| 19 | 1:160 | 1:160 |
| 20 | 1:640 | 1:320 |

The table shows two measurements for each of the twenty samples. The first measurement column reflects measurement by the present system. The second measurement reflects measurement by conventional titration. Both measurements were obtained from the same slide which contained a conventional titer of the sample. The first well of the sample titer, which contained a 1:40 dilution, was used to obtain the endpoint using the subject titration emulation method. The conventional endpoint was obtained using standard endpoint titration criteria.

Sample 11 in the above table had an endpoint of 1:320 using the subject method and a conventional endpoint of 1:80. This two-fold dilution difference is outside acceptable measurement criteria. However, a repeat measurement of this sample had an endpoint of 1:160 as determined by the subject system and a conventional endpoint of 1:80, which is acceptable.

Using the standard clinical lab criteria for acceptable measurement (plus or minus one dilution), 19 of the 20 samples measured in the initial phase of the study are acceptable, only one sample showed a discrepancy. This is a 19/20=0.95 correlation. A repeat measurement of the single discrepancy (Sample 11 in the above table) brought it within the acceptable measurement criteria. Effective 20/20 or 1.00 correlation.

EXAMPLE 2

An embodiment of the subject system was built in accordance with the description provided above in the specification. Key components were:

486 PC compatible computer

Kontron frame grabber board

Optronics DEI-470 low-light RGB camera with serial interface

Zeiss Axioskop with HBO 100 W/2 fluorescence package and trinocular head

Filter set for FITC stain

Plan-NEOFLUAR 40x/0.75 objective

Although normal operation of the titration emulation system requires a single trained ANA technologist to operate both the microscope and computer, to obtain unbiased data for the following experiment, the responsibilities of the ANA technologist were divided between two people, one acting as a technologist and the second acting as a technician. As can well be appreciated, a single trained user will improve performance and be able to detect any operating errors if they occur.

The technologist operated the microscope, selecting fields of view, and recording data. The technologist moved randomly between the appropriate wells of each slide, selecting a representative field of view for each sample to be measured.

The technician operated the computer and selected the image endpoints. The technician was completely unaware of which well was being processed so as to be as objective and consistent as possible in selecting the image endpoints for each sample.

Communication between the technologist and technician was limited to coordinating measurement data acquisition and reporting measurement data for each sample in the form of an image titer endpoint.

The FANA slides used in this test were processed as standard ANA slides with no counterstain. The set of 6 slides were labeled: A1, A2, B1, B2, C1, C2. There were 2 slides (1 and 2) for each of 3 patients (A, B, and C).

| Patient | Report Pattern | Reported Titer |
|---|---|---|
| A | smooth (homogeneous) | 1:2560 |
| B | smooth (homogeneous) | 1:5120 (or greater) |
| C | smooth (homogeneous) | 1:2560 |

For routine samples, titration is only taken out to the 1:1280 dilution. It is acceptable in practice to report titers up to 2 dilutions beyond the last physical titer, based on the technologist's perception of the fluorescent intensity observed at the 1:1280 dilution. Therefore the actual titer of these so-called "high-titer patients" may vary from the reported titer. In particular, patient B had unusually strong fluorescence even at the 1:1280 dilution, but was reported as 1:5120 due to the +2 dilution rule.

Each slide in the test set had the following layout:

| Well | Sample |
|---|---|
| + | patient 1:40 |
| 1 | patient 1:40 |
| 2 | patient 1:80 |
| 3 | patient 1:160 |
| 4 | patient 1:320 |
| 5 | pqtient 1:640 |
| 6 | patient 1:1280 |
| 7 | patient 1:2560 |
| 8 | patient 1:5120 |
| 9 | (blank) |
| 10 | (blank) |
| — | negative control |

To minimize the negative effect of drying, each slide in the slide set was quickly screened for usability. Only one slide (C1) was deemed unusable due to excessive air bubbles and premature drying. This slide was not used in the study.

For this study, the system was setup for the FANA procedure measuring endpoint titration in terms of dilution, ranging from 1:40 to 1:5120. The following table shows the calibration settings used for this study.

| Image | Exposure Time (sec) | Brightness | Contrast |
|---|---|---|---|
| 1 | ¼ | 0 | 0 |
| 2 | ¼ | −3 | 0 |
| 3 | ¼ | −6 | 0 |
| 4 | ¼ | −9 | 0 |
| 5 | ⅛ | 0 | 0 |
| 6 | ⅛ | −3 | 0 |
| 7 | ⅛ | −6 | 0 |
| 8 | ⅛ | −9 | 0 |
| 9 | 1/15 | 0 | 0 |
| 10 | 1/15 | −3 | 0 |
| 11 | 1/15 | −6 | 0 |
| 12 | 1/15 | −9 | 0 |
| 13 | 1/30 | 0 | 0 |
| 14 | 1/30 | −3 | 0 |
| 15 | 1/30 | −6 | 0 |
| 16 | 1/30 | −9 | 0 |

The following table shows the measurement label data used for this study. These labels represent titration endpoints.

| Image | Label |
|---|---|
| 0 | Negative |
| 1 | 1:40 |
| 2 | 1:80 |
| 3 | 1:160 |
| 4 | 1:320 |
| 5 | 1:640 |
| 6 | 1:1280 |
| 7 | 1:2560 |
| 8 | 1:5120 |
| 9 | Offscale |

Calibration

For each study phase, one slide was selected for calibration, with the serial dilution samples in wells 1–8 being used as standards. The relationship between the wells and titers is dependent on the ANA concentration of the initial serum. For example, if the initial serum has a known ANA concentration of 1:2560 in terms of endpoint titration, then well 1 (1:40 dilution assuming a screening dilution of 1:40 is used for measurement) is used as a standard for 1:2560, well 2 (1:80 dilution) is used as a standard for 1:1280, . . . , well 7 (1:2560 dilution) is used as standard for 1:40. Well 8 (1:5120) is negative and therefore not used as standard. Of course, different screening dilutions could be calibrated for, if desired.

In the calibration data tables below, Well is the label of the physical well used to represent the standard for the specified Titer. The Actual and Fit values are calibration image reference numbers (1–16) that correspond to the camera settings in the calibration settings table above. The Actual value is the measured image endpoint. The Fit value is the endpoint value after performing a linear fit on the calibration data.

Measurement

For each study phase, several slides were selected for measurement. The serial dilution samples in wells 1–8 are used as patient samples for measurement. The relationship between wells and titers is dependent upon ANA concentration of the initial serum (in the manner described above). The difference between calibration and measurement is that the samples on the measurement slides are used to simulate patients with various initial ANA concentrations instead of calibration standards.

In the measurement data tables below, columns represent wells of the measurement slide having associated simulated titer endpoints based on the assumed initial sample endpoint. Rows are measured endpoints using the calibrated titration emulation system. The numbers in the table are counts. The diagonal cells of the table are expected measurements. The cells above and below the diagonal are also acceptable measurements. A good correlation between measured and actual endpoints would have high counts close to the diagonal.

Evaluation

In conventional titration, the benchmark for acceptable measurement is plus/minus one dilution of the actual endpoint. For example, if the actual ANA concentration of a sample has an endpoint of 1:320, then acceptable measurements are 1:160–1:640. Since there is currently no calibration step for conventional titration, the only way to ensure consistency is repeated measurement and cross-correlation between technologists.

The data described below were evaluated by calculating an acceptable measurement hit ratio. This ratio is obtained by counting the number of acceptable measurements, according to the clinical laboratory criteria, and dividing this number by the total number of measurements. In the data tables below, acceptable measurements appear along the diagonal.

Study Phase I

For the first phase of the test it was assumed that the reported titers of patients A, B, and C were correct.

Slide A1 was used for calibration and slides A2, B2, and C2 were measured.

Calibration data for slide A 1:

| Well | Titer | Actual | Fit |
|---|---|---|---|
| 7 | 1:40 | 3 | 3 |
| 6 | 1:80 | 4 | 4 |
| 5 | 1:160 | 6 | 5 |
| 4 | 1:320 | 6 | 6 |
| 3 | 1:640 | 7 | 7 |
| 2 | 1:1280 | 9 | 8 |
| 1 | 1:2560 | 8 | 9 |
| (none) | 1:5120 | (skip) | 10 |

Measurement data for slide A2 (hit ratio = 32/32 = 1.00):

| Well | −, 8 | 7 | 6 | 5 | 4 | 3 | 2 | +, 1 |
|---|---|---|---|---|---|---|---|---|
|  | Neg | 1:40 | 1:80 | 1:160 | 1:320 | 1:640 | 1:1280 | 1:2560 |
| Neg | *4 | † | | | | | | |
| 1:40 | † | *4 | †1 | | | | | |
| 1:80 | | † | * | † | | | | |
| 1:160 | | | †3 | *1 | † | | | |
| 1:320 | | | | †3 | *3 | †1 | | |
| 1:640 | | | | | †1 | *2 | †1 | |
| 1:1280 | | | | | | †1 | *2 | † |
| 1:2560 | | | | | | | †1 | *4 |
| 1:5120 | | | | | | | | † |
| Off | | | | | | | | |

Measurement data for slide B2 (hit ratio = 14/36 = 0.39):

| Well | − | 8 | 7 | 6 | 5 | 4 | 3 | 2 | 1 |
|---|---|---|---|---|---|---|---|---|---|
|  | Neg | 1:40 | 1:80 | 1:160 | 1:320 | 1:640 | 1:1280 | 1:2560 | 1:5120 |
| Neg | * | † | | | | | | | |
| 1:40 | †2 | * | † | | | | | | |
| 1:80 | | † | * | † | | | | | |
| 1:160 | 2 | | † | * | † | | | | |
| 1:320 | | 3 | 1 | † | * | † | | | |
| 1:640 | | 1 | | | † | * | †1 | | |
| 1:1280 | | | 2 | | | † | * | † | |
| 1:2560 | | | 1 | 4 | 4 | 4 | †3 | *3 | † |
| 1:5120 | | | | | | | | †1 | *2 |
| Off | | | | | | | | | †2 |

Measurement data for slide C2 (hit ratio = 24/32 = 0.75)

| Well | −, 8 | 7 | 6 | 5 | 4 | 3 | 2 | +, 1 |
|---|---|---|---|---|---|---|---|---|
|  | Neg | 1:40 | 1:80 | 1:160 | 1:320 | 1:640 | 1:1280 | 1:2560 |
| Neg | *2 | † | | | | | | |
| 1:40 | †2 | * | † | | | | | |
| 1:80 | | † | * | † | | | | |
| 1:160 | | 4 | †4 | * | † | | | |
| 1:320 | | | | †1 | * | † | | |
| 1:640 | | | | 1 | †4 | *3 | † | |
| 1:1280 | | | | | 2 | † | * | † |
| 1:2560 | | | | | | 1 | †4 | *3 |
| 1:5120 | | | | | | | | †1 |
| Off | | | | | | | | |

As used herein, * indicates the correct value; † indicates values that are within one dilution (+1 or −1) of the correct value.

Data Evaluation

The best-fit calibration line obtained from slide A1 was unexpectedly flat and low in terms of calibration image reference values (3–10, single increments). However, the perfect hit ratio of 1.00 associated with the measurement of slide A2 demonstrated excellent correlation between calibration and measurement for patient A.

The low hit ratio of 0.39 associated with the measurement of slide B2 suggested something wrong with the measuring capability of the calibrated system. The data appear to follow a parallel line approximately 2 dilutions below the diagonal and saturates at the 1:2560 measurement level. This saturation point indicates that samples were overexposed during the image acquisition step, causing sample fading and resulting in less than optimal measuring capability at high titers.

The hit ratio of 0.75 associated with the measurement of slide C2 suggested a mild measurement problem with the calibrated system. These data appear to follow a parallel approximately 1 dilution below the diagonal for the duration of the calibrated measurement range, and brought into question the assumptions regarding the actual endpoints of patients A, B, and C. To test this hypothesis, study phase 2 was performed using corrected patient endpoints based on the data obtained in phase 1.

Study Phase 2

In the second phase of the test the following patient endpoints were assumed based on the results of phase 1:

A: 1:1280
B: 20480
C: 1:2560

Slide C2 was used for calibration and slides A2, B2, and B1 were measured.

Calibration data for slide C2:

| Well | Titer | Actual | Fit |
|---|---|---|---|
| 7 | 1:40 | 4 | 4 |
| 6 | 1:80 | 5 | 5 |
| 5 | 1:160 | 7 | 6 |
| 4 | 1:320 | 7 | 7 |
| 3 | 1:640 | 8 | 9 |
| 2 | 1:1280 | 10 | 10 |
| 1 | 1:2560 | 11 | 11 |
| (none) | 1:5120 | (skip) | 12 |

Measurement data for slide A2 (hit ratio=28/28=1.00):

| Well | −, 8, 7 | 6 | 5 | 4 | 3 | 2 | +, 1 |
|---|---|---|---|---|---|---|---|
| | Neg | 1:40 | 1:80 | 1:160 | 1:320 | 1:640 | 1:1280 |
| Neg | *4 | † | | | | | |
| 1:40 | † | * | † | | | | |
| 1:80 | | †4 | * | † | | | |
| 1:160 | | | †4 | *2 | †2 | | |
| 1:320 | | | | †2 | *2 | †1 | |
| 1:640 | | | | | † | *3 | †1 |
| 1:1280 | | | | | | † | *2 |
| 1:2560 | | | | | | | †1 |
| 1:5120 | | | | | | | |
| Off | | | | | | | |

Measurement data for slide B2 (hit ratio=28/32=0.88):

| Well | − | 8 | 7 | 6 | 5 | 4 | 3 | 2, 1, + |
|---|---|---|---|---|---|---|---|---|
| | Neg | 1:160 | 1:320 | 1:640 | 1:1280 | 1:2560 | 1:5120 | Off |
| Neg | *2 | | | | | | | |
| 1:40 | † | | | | | | | |
| 1:80 | 2 | † | | | | | | |
| 1:160 | | *1 | † | | | | | |
| 1:320 | | †2 | *1 | †1 | | | | |
| 1:640 | | 1 | †2 | *1 | †1 | | | |
| 1:1280 | | | 1 | †2 | *3 | †2 | | |
| 1:2560 | | | | | | *2 | †2 | 2 |
| 1:5120 | | | | | | | *2 | †1 |
| Off | | | | | | | † | *1 |

Measurement data for slide B1 (hit ratio=25/32=0.78):

| Well | − | 8 | 7 | 6 | 5 | 4 | 3 | 2, 1, + |
|---|---|---|---|---|---|---|---|---|
|  | Neg | 1:160 | 1:320 | 1:640 | 1:1280 | 1:2560 | 1:5120 | Off |
| Neg | *4 | | | | | | | |
| 1:40 | † | | | | | | | |
| 1:80 | | † | | | | | | |
| 1:160 | | * | † | | | | | |
| 1:320 | | †2 | * | † | | | | |
| 1:640 | | 2 | †3 | 4 | †1 | | | |
| 1:1280 | | | 1 | † | *2 | † | | 1 |
| 1:2560 | | | | | †1 | *4 | †3 | 3 |
| 1:5120 | | | | | | † | *1 | † |
| Off | | | | | | | † | * |

Data Evaluation

The best-fit calibration line obtained from slide C2 was slightly steeper and higher (4–12, mostly single increments) compared to the phase 1 calibration on slide A1. This is consistent with the hypothesis regarding the patient endpoints (A: 1:1280, B: 1:2560).

The perfect hit ratio of 1.00 associated with the measurement of slide A2 demonstrated excellent correlation between calibration and measurement between patients C and A, respectively.

The hit ratios of 0.88 and 0.78 for slides B2 and B1, respectively, are both improvements over the patient measurement of phase 1 (hit ratio 0.39). These data suggest a slight saturation and fading problem with high-titer patients such as patient B (1:20480 and greater). However, at the conclusion of the slide B1 measurement it was noticed that the wells of the test slides had begun to dry (5 hours). In particular, the + (plus sign), 1 and 2, wells of the slide B1 had lost their seal and were hazed over. If these wells are removed from the data, B1 would have a hit ratio of 25/28=0.89.

The phase 2 data demonstrate good overall correlation between calibration and measurement data.

Conclusion

The titration emulation system demonstrated good overall calibration and measurement performance with the corrections to the patient endpoints of phase 1 data and assumptions in phase 2 being confirmed by the laboratory. Of course, measurements are more accurate and consistent utilizing a calibrator produced specifically for the titration emulation system.

A preferred embodiment of the present invention employs an automatic shutter. An automatic shutter, preferably under software control, minimizes exposure time for each sample and improves the performance of both calibration and measurement. As evidenced by the data associated with super-high-titer patient B, there is a negative effect of sample overexposure and consequential fading during the image acquisition step in the absence of a shutter.

It is also possible to improve performance by fine-tuning the calibration settings. By optimizing the calibration settings for the appropriate level of exposure times, a more uniform image gradient can be achieved during calibration, improving the accuracy of the measurement.

It should be also noted that the people involved in this study intentionally were not trained as ANA technologists (to minimize human influence), and that a single trained ANA technologist would have produced more accurate and consistent results.

The invention has been described in terms of its preferred embodiments. These embodiments are set forth to aid in the better understanding of the subject invention. As it will become apparent after reading the specification, numerous alternative embodiments will become obvious to those skilled in the art. For example, digital signals could be directly compared to eliminate human factors, calibration standards could be inputted as digital signals, color could be used as a visualization parameter, etc. These variations are to be considered within the scope and spirit of the invention which is only to be limited by the claims that follow and their equivalents.

What is claimed is:

1. A titration emulation system for titrating a sample, said sample having a titration endpoint, which comprises:

(a) a detector for visualizing the sample in accordance with predetermined visualization parameters, the parameters for each visualization forming a setting;

(b) means for generating a digital visualization signal corresponding to the detector's visualization of the sample;

(c) means for altering the visualization parameters used to generate the digital visualization signal;

(d) means for storing the settings for the visualization parameters; each of said stored settings corresponding to a predetermined titration endpoint, (e) means for modifying the digital visualization signal by altering the visualization parameters according to the settings stored by the storage means; and (f) computer means for evaluating the modified digital visualization signal so as to determine the titration endpoint of the sample.

2. The system in accordance with claim 1, wherein the detector is a digital video camera.

3. The system in accordance with claim 1, wherein the detector is an analog video camera.

4. The system of claim 3 further comprising means for converting analog signals to digital signals.

5. The system in accordance with claim 1 further comprising a microscope which is optically coupled with the detector.

6. The system in accordance with claim 5, wherein the microscope is a fluorescence microscope.

7. The system in accordance with claim 1, wherein means for generating a digital signal comprise an imaging board.

8. A method for titration emulation of a sample solution, which comprises:

(a) providing a plurality of calibration standards, each containing a different known concentration of a visualizable material;

(b) visualizing the visualizable material contained within each calibration standard, the parameters of each visualization forming a setting;

(c) for each calibration standard, altering the visualization of the material contained within the calibration standard by adjusting at least one parameter of the visualization of the calibration standard until the point where the visualizable material within the calibration standard can no longer be visualized within the solution;

(d) visualizing the visualizable material within a sample solution having an unknown concentration of the visualizable material using each of the plurality of calibration standards, to generate a number of modified visualizations which correspond to the concentration of the calibration standard to which each modified visualization relates; and (e) correlating the modified visualization which represents the point at which the visualizable material in the sample solution can no longer be visualized with the corresponding concentration of the calibration standard to which the modified visualization relates, thereby determining the titration endpoint of the sample solution.

9. The method according to claim 8, wherein the providing a plurality of calibration standards in step (a) comprises (i) providing a plurality of standard solutions, each having a different concentration of the visualizable material, (ii) reducing the concentration of the visualizable material within each standard solution until the concentration of the visualizable material is such that the visualizable material can no longer be visualized within each resulting solution, and (iii) determining the concentration at which the visualizable material can no longer be visualized within each of the resulting solutions.

10. The method according to claim 8, wherein the visualizable material is a fluorescent material.

11. The method according to claim 8, wherein the parameters of the visualization comprise exposure time, contrast and brightness.

12. The method according to claim 8, wherein the settings corresponding to the plurality of calibration standards are interpolated or extrapolated from the settings for each calibration standard visualized.

13. The method according to claim 8, wherein the plurality of calibration standards in step (a) is provided by serial dilution of a visualizable material of known concentration.

14. The method according to claim 8, wherein the parameters of the visualization comprise an exposure time value.

15. The method according to claim 14, wherein the exposure time value comprises an exposure time and analog adjustments to the exposure time.

16. The method according to claim 14, wherein the exposure time value comprises an exposure time and digital adjustments to the exposure time.

17. An imaging system usable for emulating a titration of a sample, said sample having a titration endpoint, which comprises:

(a) a detector for visualizing the sample in accordance with predetermined visualization parameters, the parameters for each visualization forming a setting;

(b) means for generating a digital visualization signal corresponding to the detector's visualization of the sample;

(c) means for altering the visualization parameters used to generate the digital visualization signal;

(d) means for storing the settings for the visualization parameters; each of said stored settings corresponding to a predetermined titration endpoint, (e) means for modifying the digital visualization signal by altering the visualization parameters according to the settings stored by the storage means; and (f) means for displaying the modified digital visualization signal to a human user so as to enable the user to determine the titration endpoint of the sample.

18. The system in accordance with claim 17, wherein the detector is a digital video camera.

19. The system in accordance with claim 17, wherein the detector is an analog video camera.

20. The system of claim 19 further comprising means for converting analog signals to digital signals.

21. The system in accordance with claim 17 further comprising a microscope which is optically coupled with the detector.

22. The system in accordance with claim 21, wherein the microscope is a fluorescence microscope.

23. The system in accordance with claim 17, wherein means for generating a digital signal comprise an imaging board.

* * * * *